United States Patent
Jeong et al.

(10) Patent No.: US 6,913,574 B2
(45) Date of Patent: Jul. 5, 2005

(54) METHOD AND APPARATUS FOR MEASURING ELASTIC CHARACTERISTICS OF A MEDIUM BY USING ULTRASOUND IMAGES

(75) Inventors: Mok-Kun Jeong, Seoul (KR); Sung-Jae Kwon, Seoul (KR)

(73) Assignee: Madison Co., Ltd., Hongchun-gun (KR)

(*) Notice: Subject to any disclaimer, the term of this patent is extended or adjusted under 35 U.S.C. 154(b) by 26 days.

(21) Appl. No.: 10/611,954

(22) Filed: Jul. 3, 2003

(65) Prior Publication Data

US 2004/0006270 A1 Jan. 8, 2004

(30) Foreign Application Priority Data

Jul. 5, 2002 (KR) ................................ 10-2002-0038894

(51) Int. Cl.[7] .................................................. A61B 8/00
(52) U.S. Cl. ...................................... 600/438; 600/443
(58) Field of Search ................................ 600/438, 443, 600/447, 587; 73/573–575, 578–579

(56) References Cited

U.S. PATENT DOCUMENTS 5,474,070 A * 12/1995 Ophir et al. ................ 600/437
5,839,441 A    11/1998 Steinberg
5,876,342 A *  3/1999 Chen et al. ................. 600/443
6,558,324 B1 * 5/2003 Von Behren et al. ....... 600/440

FOREIGN PATENT DOCUMENTS

GB        2279743 A  *  1/1995  ........... G01S/15/89

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

A method and apparatus for measuring the elastic characteristics of a medium by estimating variations in the speckle patterns in ultrasound images. The method for measuring the elastic characteristics of a medium comprises the steps of applying vibrations to the medium; acquiring a plurality of ultrasound image frames of the medium; estimating a variation in brightness of the speckle pattern over the plurality of ultrasound image frames; and measuring the elastic characteristics of the medium based on the estimated brightness variation. The apparatus for measuring the elastic characteristics of a medium comprises a vibrator for applying vibrations to the medium; transducers for acquiring a plurality of ultrasound image frames of the medium; a device for estimating a variation in brightness of a speckle pattern over the plurality of ultrasound image frames; and a device for measuring the elastic characteristics of the medium based on the estimated brightness vibration.

8 Claims, 5 Drawing Sheets

Transducers

Sample Volume

METHOD AND APPARATUS FOR MEASURING ELASTIC CHARACTERISTICS OF A MEDIUM BY USING ULTRASOUND IMAGES

FIELD OF THE INVENTION

The present invention relates generally to the area of ultrasound signal processing, and more particularly, to a method and apparatus for measuring the elastic characteristics of a medium by estimating variations of speckle patterns in ultrasounds images.

BACKGROUND OF THE INVENTION

Ultrasound imaging apparatuses are widely used, for medical diagnosis purposes, to obtain an image showing the internal organs of a human body. The ultrasound imaging apparatus transmits ultrasound signals toward a target object to be diagnosed, and utilizes the echo signals reflected from the target object to obtain an image showing the desired target object. One of the obstacles encountered with a conventional ultrasound imaging apparatus in visualizing pathological tissues, such as tumors and cancerous tissues, is that if reflectivity between the pathological tissues and the neighboring tissues are not significantly different, then the conventional ultrasound imaging apparatus cannot provide a clear enough image of the pathological tissues for diagnosis. Conventionally, to overcome the above obstacle, a method of visualizing the elastic characteristics of an entire medium, including the pathological tissue and its neighboring area, is used to discriminate between the pathological tissue and the normal tissue. The method exploits the pathological tissue's property of having a greater stiffness than the neighboring normal tissues.

Two kinds of methods for measuring the elastic characteristics of a medium are known in the art: one of the methods is to externally apply pressure to a medium of interest, measure the physical displacement of the medium, and calculate the local displacement from the pressure applied to the medium; and another exploits the difference in wave transmission properties between a stiff medium and a soft medium, and consists of the steps of applying low frequency vibrational forces to a medium and visualizing movement of the applied low frequency wave. However, all these methods have drawbacks as explained below.

In the first method, a relative displacement must be estimated between the echo signals received in response to transmission of an ultrasound signal to the medium after applying pressure thereto and before applying pressure to the medium, in order to diagnose if the medium is pathological tissue. Preferably, the pressure applied to the medium is increased since accurate diagnosis requires information on displacements in response to a wide range of pressures. However, if the pressure is increased, the correlation between the echo signals before and after applying pressure decreases, such that correctly identifying the displacement is difficult. As a result, discriminating between normal and pathological tissues is not viable. Further, in both methods, calculating waveform displacements or phase changes based on RF or envelope data, relating to the transmitted and received ultrasound signals is necessary. Since these methods need to compute signal correlations, they require complex hardware having high-speed signal processing capability, and thus the costs associated with these methods is high.

Accordingly, a need for a new and improved method and apparatus for measuring the elastic characteristics of a medium exists in the art.

SUMMARY OF THE INVENTION

It is therefore an object of the present invention to provide a method and apparatus for measuring the elastic characteristics of a medium by estimating variations of speckle patterns in ultrasound images.

It is another object of the present invention to provide a method and apparatus of measuring the elastic characteristics of a medium, which can minimize the required number of frame memories and the required amount of calculation.

According to one aspect of the present invention, a method for measuring elastic characteristics of a medium is provided, which comprises the steps of applying vibrations to the medium; acquiring a plurality of ultrasound image frames of the medium; estimating a variation in brightness of a speckle pattern over the plurality of ultrasound image frames; and measuring the elastic characteristics of the medium based on the estimated brightness variation.

According to another aspect of the present invention, an apparatus for measuring elastic characteristics of a medium is provided, which comprises a vibrator for applying vibrations to the medium; transducers for acquiring a plurality of ultrasound image frames of the medium; means for estimating a variation in brightness of a speckle pattern over the plurality of ultrasound image frames; and means for measuring the elastic characteristics of the medium based on the estimated brightness vibration.

BRIEF DESCRIPTION OF DRAWINGS

The features of the present invention, which are believed to be novel, are set forth with particularity in the appended claims. The present invention, both as to its organization and manner of operation, together with further objects and advantages thereof, may best be understood with reference to the following description, taken in conjunction with the accompanying drawings.

DETAILED DESCRIPTION OF THE PRESENT INVENTION

Figure 1:
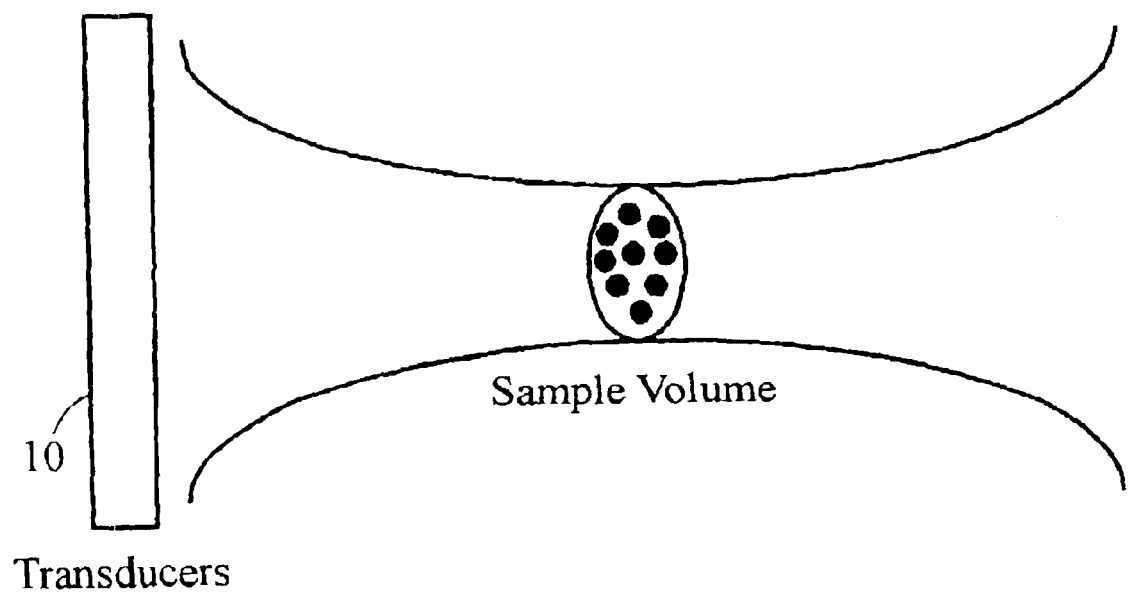
FIG. 1 shows a distribution of reflectors within a sample volume of ultrasonic beams transmitted from a transducer array.

Ultrasound images generally include a particular noise pattern called a "speckle pattern." For example, a B-mode ultrasound image of a soft tissue within a human body has a plurality of granular speckles. The speckles are generated by the coherent nature of the ultrasound imaging system and are a detriment to obtaining high-resolution ultrasound images. More specifically, the speckles are generated because the signals reflected from the reflectors distributed within ultrasound beams are non-uniformly superimposed. Therefore, as shown in FIG. 1, if the distribution of reflectors within a sample volume of ultrasound beams from the array transducers varies, then the speckle pattern varies accordingly. Therefore, if a vibrational force is applied to soft tissue of the human body to vibrate the tissue, the speckle pattern in the ultrasound image changes. Thus, the ultrasound image brightness changes.

Figure 2:
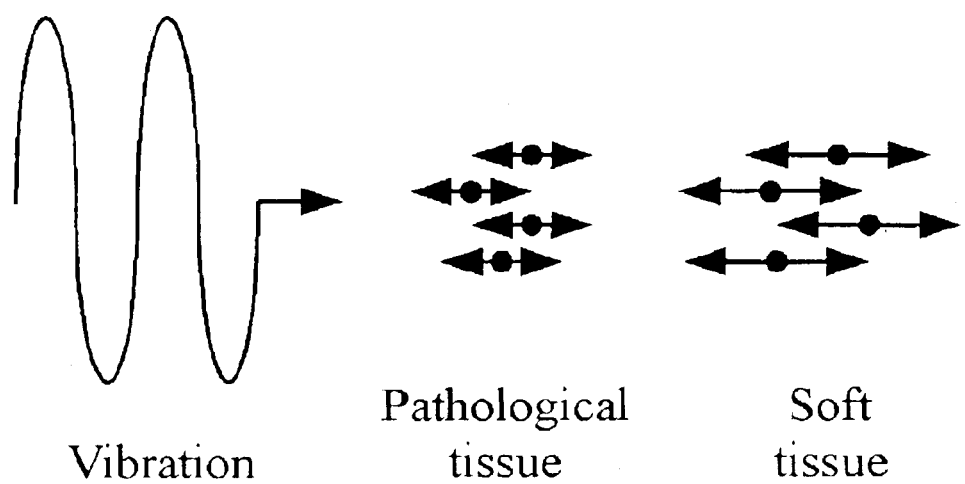
FIG. 2 is a view to illustrate a variation of a distribution of reflectors within a tissue in response to an applied vibration.

As mentioned before, the stiffness of pathological tissue is greater than that of normal soft tissue. Further, in response to an applied vibration, the change in distribution of reflectors within the tissue is inversely proportional to the stiffness of the tissue, as shown in FIG. 2. In other words, for stiff tissue, an applied vibration causes the entire tissue, including the tissue of interest, to move as a whole, such that the speckle pattern does not change much. On the other hand, for soft tissue, the applied vibration significantly changes the positions of the reflectors within the tissue. As a result, the change in the speckle pattern, in response to an applied vibration is proportional to the softness of the tissue. Based on this principle, the stiffness of the tissue may be measured.

The change in brightness of a speckle can be estimated by observing the variation of pixels situated at the same positions along the time axis in a series of B-mode ultrasound images. As an indicator of a change in brightness, a variance of brightness may be used. Alternatively, a standard deviation, which is the square root of a variance, may also be used. According to the present invention, variances of brightness for all the pixels in an image frame are calculated, and their values are displayed in real time for the measurement of the elastic characteristics of a medium. The user may arbitrarily determine the number of image frames for calculating variances. In order to obtain a more accurate estimate of the elastic characteristics of a medium, the magnitude and frequency of an applied vibrational force may be adjusted to a find a resonant frequency and magnitude.

Figure 3:
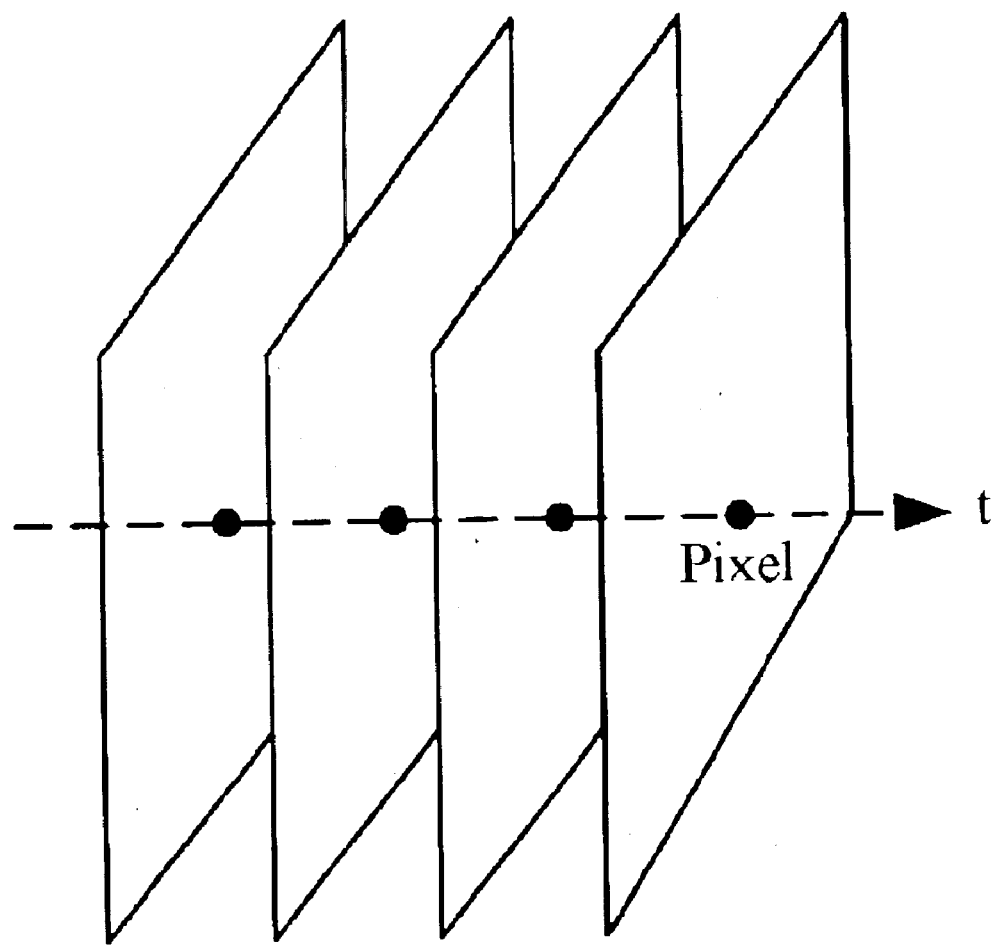
FIG. 3 illustrates pixels situated in the same position in consecutive B-mode ultrasound images.
Figure 4:
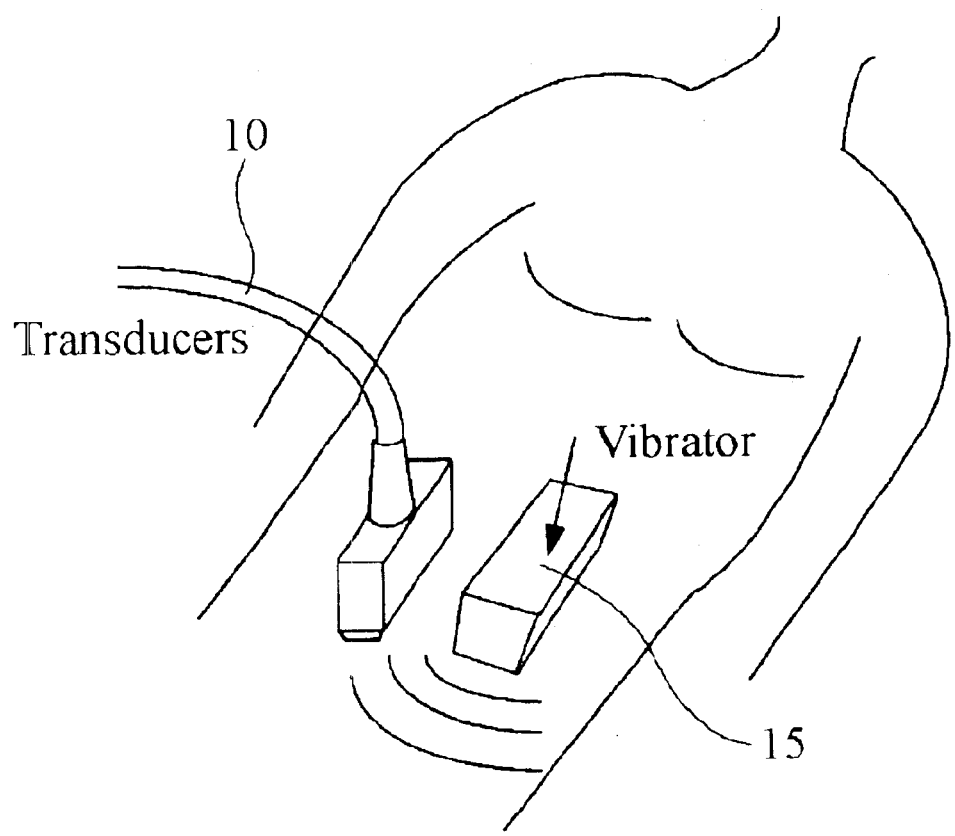
FIG. 4 is a schematic view showing a low frequency vibrator brought into contact with a human body, in accordance with the present invention.

The vibrator frequency and amplitude may be adjusted is needed. Preferably, the frequency of the vibrator is within several hundred Hertz. FIG. 4 shows a schematic view where a low frequency vibrator is brought into contact with a human body. Referring to FIG. 4, an operator diagnosing a patient applies vibrator 15 to the patient's body. As shown, the vibrations are applied in a non-invasive manner by bringing vibrator 15 into contact-with the skin of the human body and keeping transducer 10 down toward the human body. The tissue vibrates according to the force applied by vibrator 15, and as a result, scatterers consisting of the tissue move so that a plurality of different images frames as shown in FIG. 3 are obtained. Thus, the brightness of a certain pixel may continuously changes throughout the image frames.

Alternatively, an invasive method may be used to transfer the vibrational force to a medium to more precisely observe specific tissue of the human body. A needle is inserted into the medium and vibrations are transferred to the medium via the tip of the needle. Although this invasive method may be somewhat burdensome to the patient as the needle has to be inserted into the body of the patient, the advantage is that vibrations may be precisely transferred to a desired location in the body.

The speckle brightness change due to an applied vibration may be determined by calculating the brightness change of each pixel. As a measure of the brightness change, the brightness standard deviation at each pixel of an entire B mode image frame may be used. A mean $m_n(i,j)$ and a standard deviation an $\sigma_n(i,j)$ of a certain number, i.e., M, of consecutive image frames, starting from the $(n-M+1)^{th}$ frame and including up to the $n^{th}$ frame, at individual pixel points (i,j) may be expressed by Equations (1) and (2), respectively:

$$m_n(i, j) = \frac{1}{M} \sum_{k=n-M+1}^{n} x_k(i, j) \qquad \text{Eq. (1)}$$

$$\sigma_n(i, j) = \sqrt{\frac{1}{M} \sum_{k=n-M+1}^{n} [x_k(i, j) - m_n(i, j)]^2} \qquad \text{Eq. (2)}$$

wherein $x_k(i,j)$ is the brightness at pixel (i,j) of the $k^{th}$ frame, which corresponds to each pixel value displayed on a monitor; and i and j are horizontal and vertical pixel indices, respectively.

In calculating brightness variances for pixels in the image frames, N is first assumed to be the current frame number, N−1 is the previous frame number, $X_N(i,j)$ represents a brightness value of the $(i,j)^{th}$ pixel in the $n^{th}$ frame, and $m_N(i,j)$ and $m_{N-1}(i, j)$ represent an average brightness for the $(i,j)^{th}$ pixel over the N number of frames as counted from the first frame and an average brightness for the $(i,j)^{th}$ pixel over the N−1 number of frames as counted from the first frame, respectively. $\sigma_N^2(i,j)$ and $\sigma_{N-1}^2(i,j)$ are also assumed to represent brightness variances for the $(i,j)^{th}$ pixel over the N number of frames as counted from the first frame and for the $(i,j)^{th}$ pixel over the N−1 number of frames as counted from the first frame, respectively. Then, the average brightness for the $(i,j)^{th}$ pixel, $m_N(i,j)$, and the brightness variance for the $(i, j)^{th}$ pixel, $\sigma_N^2(i,j)$, may be expressed by Equations (3) and (4), respectively:

$$m_N(i, j) = m_{N-1}(i, j) + \frac{1}{N}[x_N(i, j) - m_{N-1}(i, j)] \qquad \text{Eq. (3)}$$

$$m_N(i, j) = \frac{(N-1)m_{N-1}(i, j) + x_N(i, j)}{N}$$

$$\sigma_N^2(i, j) = \sigma_{N-1}^2(i, j) + m_{N-1}^2(i, j) + \frac{1}{N}[x_N^2(i, j) - Nm_N^2(i, j) - \sigma_{N-1}^2(i, j) - m_{N-1}^2(i, j)]. \qquad \text{Eq. (4)}$$

Equations (3) and (4) are recursive forms of Equations (1) and (2), respectively.

According to the above recursive equations, the previous average and variance values are used to calculate the current average and variance values. The initial values for the average and variance are set based on the first inputted data pursuant to the general principle used in recursive types of equations. Therefore, the average and variance in the first frame may be represented by Equation (5):

$$m_1(i, j) = \frac{x_1(i, j)}{1} = x_1(i, j) \qquad \text{Eq. (5)}$$

$$\sigma_1^2(i, j) = \frac{[x_1(i, j) - m_1(i, j)]^2}{1} = 0.$$

That is, the initial value for the average, $m_1(i,j)$, and initial value for the variance, $\sigma_1^2(i,j)$, are equal to $X_1(i,j)$ and 0, respectively. The next values for the average and variance are recursively calculated based on the next input $X_2(i,j)$. If the average and variance of brightness are recursively calculated according to above Equations (3) and (4), images showing variance values of brightness for all the pixels may be displayed at the same rate as the frame rate of the input images since the variance values are calculated upon acquisition of a new frame.

Figure 5:
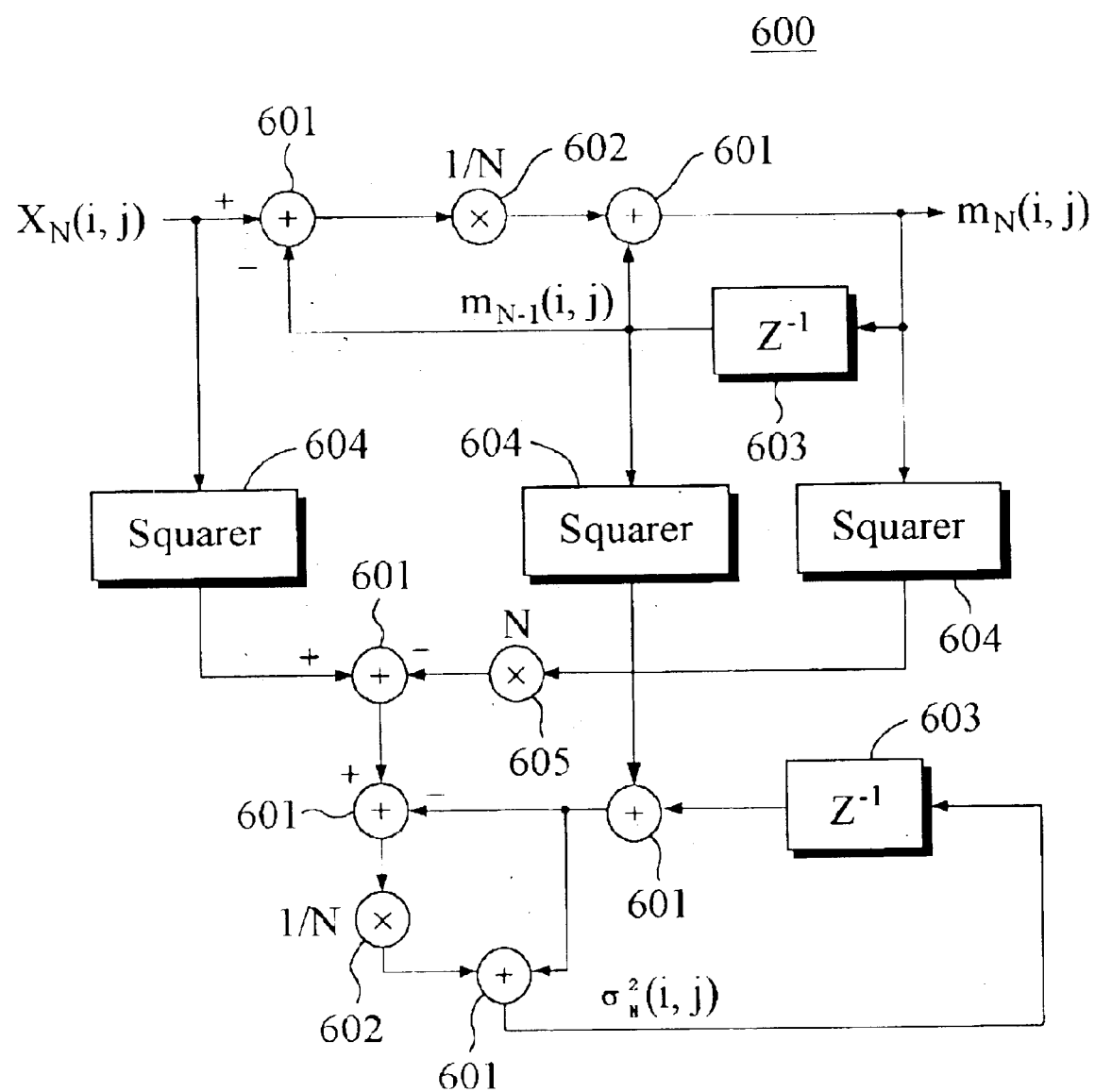
FIG. 5 is a circuit diagram for calculating variances of brightness of pixels over a plurality of image frames, in accordance with the present invention.

Referring to FIG. 5, there is shown a circuit diagram for calculating variances of brightness for pixels over a plurality of image frames, according to the above equations. As shown in FIG. 5, a circuit 600 includes a plurality of adders 601, a plurality of 1/N dividers 602, a plurality of frame delay elements 603, a plurality of squarers 604, and N-fold multiplier 605. For frame delay element 603, a frame memory may be used. The first frame delay element is used for storing the average taken up to the $(N-1)^{th}$ frame, $m_{N-1}(i,j)$, and the second frame delay element is used for storing the variance taken up to the $(N-1)^{th}$ frame, $\sigma_{N-1}^2(i,j)$. According to the structure of the circuit for calculating the variance as shown in FIG. 5, only the average and variance for each pixel in the image frame that is immediately prior to the current image frame are stored. The circuit of FIG. 5 may be implemented by either hardware or software, and is preferably mounted at the rear end of a conventional ultrasound imaging system along with the vibrator.

In order to further reduce the amount of calculations, an absolute difference between maximum and minimum values of brightness of a pixel over a predetermined frame period may be used instead of the variance, which has to be calculated at every frame timing. Assuming, for example, 15 image frames $X_1(i,j)$–$X_{15}(i,j)$, maximum and minimum values of brightness of every pixel over the 10 image frames, i.e., $\max_{1-10}(i,j)$ and $\min_{1-10}(i,j)$, may be calculated. Thereafter, a difference between the maximum and minimum values, i.e., $\text{diff}_{1-10}(i,j)=|\max_{1-10}(i,j)-\min_{1-10}(i,j)|$ may be calculated. Performing this type of calculation for every pixel results in a difference image $\text{diff}_{1-10}$, indicating the difference at every pixel position. Likewise, if the calculation is performed upon the image frames $X_2(i,j)$–$X_{11}(i,j)$, a difference image $\text{diff}_{2-11}$ may be obtained. Repeating the calculation finally results in a difference image $\text{diff}_{6-15}$. Repeating the same calculation for the next image frames $X_{16}(i,j)$, $X_{17}(i,j)$, etc., provides a difference image updated at every frame timing. According to this embodiment, an image similar to the variance image may be obtained with a reduced amount of calculation as compared to the method illustrated in FIG. 5.

As explained above, the reason why the variance of brightness over the image frames may be used as an indicator of the variation of the speckle pattern is that the variance of brightness for a certain pixel is proportional to the displacement of the scatterer located at the pixel position, and the displacement is proportional to the stiffness of the scatterer. Since pathological tissue has an increased stiffness as compared to normal soft tissue, the speckle pattern for pathological tissue does not vary much because the variances of brightness as calculated by using the above equations and the circuit shown in FIG. 5 do not vary significantly over several image frames. On the other hand, for normal soft tissue, the scatterers within the tissue move to a great extent under an applied vibration, and thus the variances of brightness calculated by using the circuit shown in FIG. 5 vary significantly over several image frames. Based on this principle, the stiffness of the tissue may be measured. For a more accurate diagnosis, the standard value for the stiffness of certain tissue must be provided so that the degree of deviation from the standard value may be used as a measure for the diagnosis.

As described in the foregoing, the elastic characteristics of a medium may be measured by calculating variances of brightness for every pixel over consecutive B-mode ultrasound images. Therefore, the operator who is diagnosing the patient may readily discern any-pathological tissue within the patient's body. According to the method and apparatus of the present invention, only acquired ultrasound images are used for the measurement, and thus software programs may be employed for such purpose. Further, since the method and apparatus of the present invention employs a recursive type of calculation, the size of the required hardware such as frame memory, amount of calculation, and the CPU load may be greatly reduced.

While particular embodiments of the present invention have been shown and described, those skilled in the art will appreciate that changes and modifications may be made without departing from this invention in its broader aspects and, therefore, the aim in the appended claims is to cover all such changes and modifications, as fall within the true spirit and scope of this invention.

What is claimed is:

1. A method for measuring elastic characteristics of a medium, comprising:

applying vibrations to the medium;

acquiring an N number of ultrasound image frames of the medium;

estimating a variation in brightness of a speckle pattern over the N number of ultrasound image frames by calculating an average brightness and variance in brightness for every pixel over the N number of ultrasound image frames, wherein the average brightness and variance in brightness are calculated by the following equations:

$$m_N(i, j) = m_{N-1}(i, j) + \frac{1}{N}[x_N(i, j) - m_{N-1}(i, j)]$$

$$\sigma_N^2(i, j) = \sigma_{N-1}^2(i, j) + m_{N-1}^2(i, j) + \frac{1}{N}[x_N^2(i, j) - Nm_N^2(i, j) - \sigma_{N-1}^2(i, j) - m_{N-1}^2(i, j)]$$

wherein N is a current frame number, N–1 is a previous frame number, $X_N(i,j)$ represents a brightness value of the $(i,j)^{th}$ pixel in the $n^{th}$ frame, $m_N(i,j)$ and $m_{N-1}(i,j)$ represent an average brightness for the $(i,j)^{th}$ pixel over the N number of frames as counted from the first frame and an average brightness for the $(i,j)^{th}$ pixel over the N–1 number of frames as counted from the first frame, respectively, and σhd $N^2(i,j)$ and σhd $N-1^2(i,j)$ represent a variance in brightness for the $(i,j)^{th}$ pixel over the N number of frames as counted from the first frame and a variance in brightness for the $(i,j)^{th}$ pixel over the N–1 number of frames as counted from the first frame, respectively; and measuring the elastic characteristics of the medium based on the estimated brightness variation.

2. The method according to claim 1, wherein a first frame delay element is used for storing the average brightness taken up to the $(N-1)^{th}$ frame, $m_{N-1}(i,j)$, and a second frame delay element is used for storing the variance in brightness taken up to the $(N-1)^{th}$ frame σhd $N-1^2(i,j)$.

3. The method according to claim 1, wherein the estimating includes finding maximum and minimum values of brightness for each pixel over the N number of ultrasound image frames and calculating an absolute difference value between the maximum and minimum values.

4. The method according to claim 1, wherein the average brightness and the variance in brightness are calculated by recursion.

5. An apparatus for measuring elastic characteristics of a medium, comprising:
- a vibrator for applying vibrations to the medium;
- transducers for acquiring an N number of ultrasound image frames of the medium;
- means for estimating a variation in brightness of a speckle pattern over the N number of ultrasound image frames, wherein the means for estimating calculates an average brightness and variance in brightness for every pixel over the N number of ultrasound image frames by using the following equations:

$$m_N(i, j) = m_{N-1}(i, j) + \frac{1}{N}[x_N(i, j) - m_{N-1}(i, j)]$$

$$\sigma_N^2(i, j) = \sigma_{N-1}^2(i, j) + m_{N-1}^2(i, j) + \frac{1}{N}[x_N^2(i, j) - Nm_N^2(i, j) - \sigma_{N-1}^2(i, j) - m_{N-1}^2(i, j)]$$

wherein N is a current frame number, N−1 is a previous frame number, $X_N(i,j)$ represents a brightness value of the $(i,j)^{th}$ pixel in the $n^{th}$ frame, $m_N(i,j)$ and $m_{N-1}(i,j)$ represent an average brightness for the $(i,j)^{th}$ pixel over the N number of frames as counted from the first frame and an average brightness for the $(i,j)^{th}$ pixel over the N−1 number of frames as counted from the first frame, respectively, and σhd $N^2(i,j)$ and σhd $N-1^2(i,j)$ represent a variance in brightness for the $(i,j)^{th}$ pixel over the N number of frames as counted from the first frame and a variance in brightness for the $(i,j)^{th}$ pixel over the N−1 number of frames as counted from the first frame, respectively, and means for measuring the elastic characteristics of the medium based on the estimated brightness variation.

6. The apparatus according to claim 5, wherein the means for estimating further comprises first and second frame delay elements, the first frame delay element storing the average brightness taken up to the $(N-1)^{th}$ frame, $m_{N-1}(i,j)$ and the second frame delay element storing the variance in brightness taken up to the $(N-1)^{th}$ frame, σhd $N-1^2(i,j)$.

7. The apparatus according to claim 5, wherein the means for estimating finds maximum and minimum values of brightness for each pixel over the N number of ultrasound image frames and calculates an absolute difference value between the maximum and minimum values.

8. The apparatus according to claim 5, wherein the means for estimating calculates the average brightness and the variance in brightness by recursion.

* * * * *

UNITED STATES PATENT AND TRADEMARK OFFICE
CERTIFICATE OF CORRECTION

PATENT NO.     : 6,913,574 B2
DATED          : July 5, 2005
INVENTOR(S)    : Jeong et al.

It is certified that error appears in the above-identified patent and that said Letters Patent is hereby corrected as shown below:

Title page,
Item [73], Assignee, should read as follows:
-- [73], Assignee:     Medison Co., Ltd., Hongchun-gun (KR) --.

Signed and Sealed this

Fourth Day of October, 2005

JON W. DUDAS
*Director of the United States Patent and Trademark Office*